United States Patent
Laude et al.

(10) Patent No.: US 7,749,608 B2
(45) Date of Patent: *Jul. 6, 2010

(54) MOLDED POLYMER COMPRISING SILICONE AND AT LEAST ONE METAL TRACE

(75) Inventors: Lucien D. Laude, Rabastens-de-Bigorre (FR); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 294 days.

This patent is subject to a terminal disclaimer.

(21) Appl. No.: 11/810,758

(22) Filed: Jun. 6, 2007

(65) Prior Publication Data

US 2007/0292667 A1 Dec. 20, 2007

Related U.S. Application Data (60) Provisional application No. 60/811,494, filed on Jun. 6, 2006, provisional application No. 60/811,683, filed on Jun. 7, 2006.

(51) Int. Cl.
*H05K 1/09* (2006.01)

(52) U.S. Cl. .................... 428/450; 428/209; 428/447; 174/72 C; 174/72 TR; 174/254; 174/257; 174/258

(58) Field of Classification Search ............... 428/209, 428/447, 450; 174/257–259, 72 C, 72 TR, 174/254
See application file for complete search history.

(56) References Cited

U.S. PATENT DOCUMENTS

| | | | | |
|---|---|---|---|---|
| 3,168,617 A | * | 2/1965 | Richter | 174/117 FF |
| 4,604,678 A | * | 8/1986 | Hagner | 361/761 |
| 4,670,351 A | * | 6/1987 | Keane et al. | 428/549 |
| 5,109,844 A | | 5/1992 | de Juan, Jr. et al. | |
| 5,340,641 A | * | 8/1994 | Xu | 428/209 |
| 5,450,286 A | * | 9/1995 | Jacques et al. | 361/749 |
| 5,599,592 A | | 2/1997 | Laude | |
| 5,935,155 A | | 8/1999 | Humayun et al. | |
| 6,274,225 B1 | * | 8/2001 | Miyake et al. | 428/209 |
| 6,400,989 B1 | | 6/2002 | Eckmiller | |
| 6,458,157 B1 | | 10/2002 | Suaning | |
| 6,743,345 B2 | | 6/2004 | Belouet et al. | |
| 6,878,643 B2 | | 4/2005 | Krulevitch et al. | |
| 7,005,179 B2 | * | 2/2006 | Davidson et al. | 428/209 |
| 7,255,919 B2 | * | 8/2007 | Sakata et al. | 428/352 |

FOREIGN PATENT DOCUMENTS

EP 0 442 674 A2 8/1991

OTHER PUBLICATIONS

Fertigungstechnik: Folie ALS Umweltfreundliche Leiterplatten-Alternative Weka Fachzeitschriftenverlag, Poing de vol. 49, No. 11, May 2000, p. 30.

(Continued)

*Primary Examiner*—Cathy Lam
(74) *Attorney, Agent, or Firm*—Scott B. Dunbar; Gary Schnittgrund; Tomas Lendvai (57) ABSTRACT

The present invention provides a flexible electrode array, comprising a silicone containing body, at least one metal trace layer and at least one electrode pad on the surface.

8 Claims, 11 Drawing Sheets

OTHER PUBLICATIONS

M. Maghribi, et al., Stretchable Micro-Electrode Array, 2nd Annual Int. IEEE-EMBS Special Topic Conf. on Microtechnologies in Med. & Biology, May 2-4, 2002, Madison, WI, pp. 80-83.

V. Vince, et al., Biocompatibility of Platinum-Metalized Silicone Rubber: in Vivo and in Vitro Evaluation, J. Biomater. Sci. Polymer Edn. 2004, pp. 173-188, vol. 15, No. 2.

L.D. Laude, et al., Laser Metallization for Microelectronics and Bio-Applications, Photon Processing in Microelectronics and Photonics, 11, 2003, pp. 578-586, SPIE, vol. 4977.

* cited by examiner

FIG. 9A silicone

MgF$_2$-coated glass mold pieces

MgF$_2$-coated glass mold pieces

FIG. 9B silicone molded exhaust (to be severed after un-molding)

silicone cable

MOLDED POLYMER COMPRISING SILICONE AND AT LEAST ONE METAL TRACE

CROSS-REFERENCE TO RELATED APPLICATIONS

This application claims the benefit of U.S. Provisional Application No. 60/811,494, "Molded Polymer Comprising Silicone and at Least One Metal Trace and a Process of Manufacturing the Same," filed Jun. 6, 2006. Additionally this application claims the benefit of U.S. application Ser. No. 11/595,516, "Polymer Layer Comprising Silicone and at Least One Metal Trace and a Process of Manufacturing the Same", filed Nov. 10, 2006 which claims the benefit of U.S. Provisional Application No. 60/811,683, "Polymer Layer Comprising Silicone and at Least One Metal Trace and a Process of Manufacturing the Same," filed Jun. 7, 2006.

BACKGROUND OF THE INVENTION

1. Field of the Invention

The present invention relates to a silicone polymer material comprising at least one metal trace and a process of manufacturing the same.

2. Description of Related Art

In U.S. Pat. No. 5,599,592 "Process for the Metallization of Polymer Materials and Products Thereto Obtained" to Lucien D. Laude a positive metallization process for metalizing a polymer composite piece containing a polymer material and oxide particles is disclosed, the oxide particles being made of one or more oxides, comprising three successive steps. The first step consists of the irradiation of a surface area of a polymer piece to be metalized with a light beam emitted by an excimer laser. The polymer piece is made from a polymer material and oxide particles. The oxide particles are made from one or more oxides. The second step consists of immersing the irradiated polymer piece in at least one autocatalytic bath containing metal ions. The immersion induces the deposit of the metal ions onto the irradiated surface area to form a metal film on the surface area, resulting in the selective metallization of the surface area of the polymer piece. The third step consists of thermally processing the metalized polymer piece to induce diffusion of the deposited metal film into the polymer material of the polymer piece. The disclosure of U.S. Pat. No. 5,599,592 is incorporated herein by reference.

Lucien D. Laude et al. report that excimer lasers are effective tools in engraving ceramics and polymers, changing irreversibly the surface of the irradiated material, and restricting these effects to specific areas of interest. See L. D. Laude, K Kolev, Cl. Dicara and C. Dupas-Bruzek "Laser Metallization for Microelectronics for Bio-applications", Proc. of SPIE Vol. 4977 (2003), pp 578-586.

In U.S. Pat. No. 5,935,155 "Visual Prosthesis and Method of Using Same" to Mark S. Humayun et al. it is disclosed a visual prosthesis, comprising means for perceiving a visual image, said means producing a visual signal output in response thereto; retinal tissue stimulation means adapted to be operatively attached to a retina of a user; and wireless visual signal communication means for transmitting said visual signal output to said retinal tissue stimulation means.

In U.S. Pat. No. 6,878,643 "Electronic Unit integrated Into a Flexible Polymer Body" to Peter a. Krulevitch et al. it is disclosed a method of fabricating an electronic apparatus, comprising the steps of providing a silicone layer on a matrix, providing a metal layer on said silicone layer, providing a second layer of silicone on said silicone layer, providing at least one electronic unit connected to said metal layer, and removing said electronic apparatus from said matrix wherein said silicone layer and said second layer of a silicone provide a spherical silicone body.

J. Delbeke et al. demonstrate that silicone rubber biocompatibility is not altered by the metallization method as described by Laude in U.S. Pat. No. 5,599,592. See V. Cince, M. A. Thil, C. Veraart, I. M. Colin and J. Delbeke, "Biocompatibility of Platinum-Metallized Silicone Rubber: In vivo and In vitro Evaluation", *J. Biomater. Sci.* Polymer Ed, Vol. 15, No. 2, pp. 173-188 (2004).

There is a need for a soft and biocompatible polymer layer with high insulation properties containing embedded very fine metal traces.

SUMMARY OF THE INVENTION

Another aspect of the present invention is a polymer layer comprising silicone containing oxide particles of $SiO_2$, $TiO_2$, $Sb_2O_3$, $SnO_2$, $Al_2O_3$, $ZnO$, $Fe_2O_3$, $Fe_3O_4$, talc, hydroxyapatite or mixtures thereof and at least one metal trace embedded in said polymer layer.

Another aspect of the present invention is a flexible electrode array comprising silicone containing oxide particles of $SiO_2$, $TiO_2$, $Sb_2O_3$, $SnO_2$, $Al_2O_3$, $ZnO$, $Fe_2O_3$, $Fe_3O_4$, talc, hydroxyl-apatite or mixtures thereof and at least one metal trace embedded in said polymer layer.

BRIEF DESCRIPTION OF THE DRAWINGS

FIG. 1 presents the sequence of process steps for manufacturing 1-4 levels of metalized silicone layer body;

DETAILED DESCRIPTION OF THE INVENTION

The present invention preferably relates to metallization of a polymer, generally Si-based polymers. A more preferred embodiment of the present invention is the metallization of polymers with platinum. The most preferred embodiment is a polymer layer comprising at least one metal trace embedded in the polymer layer.

The preferred polymer of the present invention is a silicone containing polymer. Silicone means, in view of the present invention, any and all possible silicone elastomer formulations, silicone craft polymers, silicone copolymers, silicone-silicone copolymers, silicone-hydrocarbon copolymers, sili- cone block polymers, silicone block copolymers, silicone rubbers or mixtures thereof. Silicone, which may be comprised of polydimethylsiloxane, may contain any type and amount of additives.

The most common method for preparing silicones involves the reaction of a chlorosilane with water. This produces a hydroxyl intermediate, which condenses to form a polymer-type structure. The basic reaction sequence is represented as follows:

n is an integer >1.

Other raw materials such as alkoxysilanes can be used as well. Chlorosilanes and other silicone precursors are synthesized by a direct process, involving the reaction of elemental silicone with an alkyl halide as follows:

Silicone elastomers have high molecular weight, generally greater than 500,000 g/mol. The production of these types of materials requires difunctional precursors, which form polymer structures. Mono and tri-functional precursors form terminal structures and branched structures, respectively.

Silicone rubbers contain usually cured additives like peroxides such as benzoyl peroxide, 2,4-dichlorobenzoyl peroxide, t-butyl perbenzoate and dicumyl peroxide. Alkyl hydroperoxides and dialkyl peroxides have also been used successfully with vinyl containing silicones.

Hydrosilylation or hydrosilation is an alternative curing method for vinyl containing silicones and utilizes hydrosilane materials and platinum containing compounds for catalysts. It is a two part process requiring mixing of two separate components, with the resulting material having a limited shelf life. Curing does not produce volatiles, hence heat cured conventional silicones with high tear strengths can be cured in this way.

Reinforcing fillers are added to improve the otherwise poor tensile strength of silicones. Silica, in the form of silica fume, silica foam, or fumed silica with particle sizes in the range 10 nm to 40 nm is the most preferred filler, although carbon black has been used. Fillers do interact with silicone to produce a vulcanizate, forming a pseudo-vulcanization. This can occur either during mixing and creep hardening or in storage and bin ageing.

Fumed silica has unique properties and is commonly added to liquids/coatings and solids to improve various properties. Fumed silica has chain-like particle morphology. In liquids, the chains bond together via weak hydrogen bonds forming a three dimensional network, trapping liquid and effectively increasing the viscosity. The effect of the fumed silica can be negated by the application of a shear force for example mixing, brushing, spraying, etc., allowing the liquid to flow, level out and permit the escape of entrapped air.

One production method for the production of fumed silica involved a continuous flame hydrolysis technique. It involves the conversion of silicon tetrachloride ($SiCl_4$) to the gas phase using an oxygen hydrogen flame. It then reacts with water to yield silica ($SiO_2$) and hydrochloric acid thus:

HCl can easily be separated as it remains in the gas phase, while $SiO_2$ is solid in the form of fumed silica.

Silicone can be in large variation of shapes and forms, such as thin sheets obtained by spun coating or spray coating, foil obtained by lamination or molding, bloc molded pieces, distributed silicone, silicone mixed with thermoplastic material.

The present invention provides a cured silicone layer which has a preferred thickness of 10 μm to 80 μm, preferably 20 μm to 40 μm, where μm is a micrometer or $10^{-6}$ meters. This layer contains laser-drawn traces up to 10 μm to 20 μm traces or pads with a dimension of 100 μm to 200 μm which are filled with metalized deposit.

The present invention further provides a silicone layer which has a preferred thickness of 15 μm to 25 μm. This layer contains laser-drawn traces having a width of to 10 μm to 20 μm which are filled with metalized deposit, preferably with platinum (Pt). This layer contains a second 15 μm to 25 μm thick silicone layer covering the once metalized first silicone layer. After curing that second silicone layer an optimum silicone-to-silicone adhesion of the second silicone layer provides a fully protected cover to the metalized silicone layer. A full silicone-encapsulation of the metal traces is thereby obtained.

The present invention provides overlapping silicones with different formulations. In the previous aspects of the present invention, silicones have a formulation that contains a variable amount of fumed silica (silica foam) that serves to strengthen the polymeric structure in various ways. It also favors the electroless-metallization process and improves substantially the mechanical behavior of metalized silicone. In this aspect of the present invention, the final silicone cover remains unmetalized and serves solely for the purpose of protecting and insulating the underlying metalized silicone layers. That silicone cover may be formed with a silicone that is different from the silicone that has been used for the underlying layers. In particular, it may not contain silica foam at all and may then be more readily applied even to very small layer thickness. Therefore, a silicone cover of 15 μm to 20 μm is formed on the metalized silicone layer. The silicone cover is formed with a silica foam free silicone that is spun onto the metalized silicone before curing as described previously.

In the metallization process a non-organic powder is dispersed in any given polymer, for example polyamide. The non-organic powder is for example at least one oxide of antimony, aluminum, iron, zinc or tin. The oxide particles have variable particle sizes, preferably smaller than about 50 μm. The concentration of the oxide particles in the polymer exceeds about 1 volume percent (vol %) or 1 weight percent (wt %).

The surface of the polymer material is irradiated with the light beam emitted by a laser. The light is emitted preferably in the ultraviolet wavelength range, during a very short duration or pulse and repeated if necessary at regular time intervals. The pulsed emission has preferably high energy, for example, between 0.05 J and 1.0 J. It contains a very large number of photons. It may also operate at a wavelength below or equal to about 350 nm which corresponds to photon energy approximately equal to or larger than 3.5 eV. The desired emission may be obtained from but is not restricted to an excimer laser source emitted during about 10 ns, at a wavelength of about 248 nm which corresponds to photon energy of 5.0 eV.

The laser beam may be passed through a mask having a specific geometry, and projected upon focalization onto the surface of the material to be treated. A desired processing is obtained beyond a given energy density of about 0.5 J/cm$^2$, or fluence, and as a function of the material optical properties and the laser photon energy.

In case of pure silicone, ultraviolet (UV) laser irradiation may produce two effects that depend on both fluence and photon energy.

At 248 nm, therefore at 5 eV, the silicone undergoes partial decomposition by breaking the Si—C bonds. This results in ablation of the C-radicals but leaves unaffected the Si—O bonds of the polymer backbone.

At lower wavelengths for example at 193 nm, therefore at 6.2 eV, the silicone undergoes total decomposition by breaking both Si—C and Si—O bonds. This results in a full ablation of silicone, typically at a rate of some 0.5 µm per pulse at 0.5 mJ/cm$^2$, and irrespective of the silicone formulation.

In the case of silicone containing silica, for example silica foam, the 248 nm laser radiation has no effect on the silica particles but the 193 nm does, which leads to a complete ablation of the silicone and its silica additive.

In the second part of the process, silicone treated with the 248 nm laser is immersed in an autocatalytic bath that contains metal ions, for example $Ni^{2+}$, $Cu^{2+}$, or $Pt^{2+}$. These ions are selectively deposited and react on the partially decomposed silicone structure regardless of whether the treated silicone contains an additive, for example silica foam. The reaction between metal ions and the polymer results in covalent bonding on the Si atoms of the polymer that lost their C-radicals upon irradiation. In the absence of silica foam, metallization occurs but with a poor adhesion of the metalized silicone part. The presence of silica foam enforces substantially the metalized silicone that is obtained after laser treating at 248 nm, since silica remains unaffected at 248 nm.

In contrast, irradiating silicone at 193 nm provides a very efficient way to fully and exclusively ablate silicone, containing silica foam or not. In particular, irradiating silicone at 193 nm allows opening clean and well defined cuts, grooves, blind holes or vias through it. Silicone parts engraved by 193 nm do not metallize by immersing in an autocatalytic bath.

During immersion of the laser processed surface into the autocatalytic bath, metallization is restricted to the actual laser treated surface. The incubation time measures the period of time which is necessary to form a continuous metal film on the composite surface. After that time, the metal deposition, which is usually 10 µm to 20 µm per hour for nickel (Ni), may develop perpendicularly to the surface in a most efficient manner.

The advantages of the process of the present invention result directly from the use of an intense and pulsed ultraviolet light beam, as for instance the one emitted by an excimer laser source working at a wavelength equal or inferior to 308 nm. All other light sources working in the visible or infrared range, in pulsed or continuous regime are inactive on silicone.

The preferred irradiation source according to this invention is an excimer laser. The preferred excimer laser performs engraving at about 248 nm with partial decomposition of silicone and allows metallization. The laser pulse duration is in the range of 1 ns to 40 ns by steady or scanning irradiation. In comparison engraving below about 200 nm performs full ablation but no metallization can follow after the ablation.

A silicone layer is spun on a clean glass plate and cured in an oven. The layer may have a near constant thickness at about 40 µm across the glass substrate. The thickness depends on spinning conditions and the content of additives. The higher the content of additives is the more difficult is the spinning. This layer is then scanned with a focused 248 nm excimer laser beam working at a sufficient fluence that allows partial decomposition of the silicone material down to some 10 µm to 15 µm into the layer. The laser processed silicone layer, on its glass substrate, is further immersed in an electroless bath containing metal ions. Subsequently, the latter ions condense solely on the laser-processed areas of the silicone layer where they contribute to form metalized deposits precisely in the laser-drawn areas and remain embedded in the silicone layer without touching the glass substrate underneath.

After preparing the metalized silicone layer on a glass substrate, a second 20 µm thick silicone layer is deposited on the once metalized first silicone layer and cured in oven. An optimum silicone to silicone adhesion of the latter is thus achieved that provides a fully protected cover to the metalized silicone layer. The set of two silicone layers are then pulled from the glass substrate and materializes the full silicone-encapsulation of the once produced metal traces.

Silicones have a formulation that contains a variable amount of silica foam additive that serves to strengthen the polymeric structure in various ways. This additive or other form of silica for example fiber also favors the electroless-metallization process and improves substantially the mechanical behavior of metalized silicone. However, the final silicone cover remains un-metalized and serves solely the purpose of protecting the underlying metalized layers. The silicone cover may be formed with a silicone that is different from the one silicone that has been used for the other underlying layers. In particular, it may not contain silica at all and may then be more readily spun, even to very small layer thickness. Therefore, a silicone cover of 20 µm is formed on the last metalized silicone layer. The silicone cover is formed with a silica-free silicone that is spun onto the metalized silicone before curing as described previously.

The electroless Pt-metallization proceeds by forming a thin, so-called black metal, film and then a second step of Pt-deposition that thickens the metal layer. The second step is extremely slow, being impaired with the formation of $H_2$-bubbles (hydrogen-bubbles) on an uneven metalizing surface; bubbles that tend to obliterate the surface and limit its direct contact with the electroless bath. Accelerating this second metallization step may be performed as follows.

After initiating the second step, the silicone layer on its substrate is removed from the bath and its surface is dried for a few seconds with a hot air jet, as produced by a standard air gun. The jet cleans the surface and heats the metal deposit. The layer is then returned to the bath for a period of 5 to 10 minutes before being removed again from the bath, dried again and re-immersed in the bath. The process is repeated regularly (and may be automated) at 5 to 10 minute intervals until the necessary metal thickness has been attained. With this transient heat procedure, time reduction from 2 to 3 hours or to 30 minutes in the process of Pt-metallization is substantial and the metal deposit may attain a greater thickness than may be accessible without it.

The present invention will be further illustrated by the following exemplary explanation of the figures, but it is to be understood that the invention is not meant to be limited to the details described herein. The figures present a preferred process for producing a silicone layer containing embedded Pt traces.

FIG. 1 presents the sequence of process steps for manufacturing 1-4 levels of metalized silicone layer body. FIG. 1 shows the process of producing a 4-level metalized silicone cable containing 4 layers of Pt traces, all terminating with end Pt electrode pads on silicone cover. Alternately the metal traces and the electrode pads are comprised of ruthenium, gold, or alloys, or mixtures thereof. It presents a sequence of repeating steps (FIG. 1 steps 1-5).

(7) Preparing a layer or mold containing silicone a;

(8) Laser engraving on the surface of the silicone b;

(9) Metallizing and preparing a trace c in the engraving b;

(10) Overlaying with a top silicone layer d;

(11) Drilling via e and optionally engraving b2;

(12) Metalizing and preparing a trace c2 and a pad f.

The sequence can repeated in steps 7-17 until 4 layers of Pt traces are obtained with 4 pads g1-g4. The first level of polymer has a thickness of 30 μm to 70 μm, preferably of 45 μm to 55 μm. The metal trace has thickness of 1 μm to 20 μm, preferably of 5 μm to 15 μm. The overlaying polymer layer has a thickness of 20 μm to 40 μm, preferably of 25 μm to 35 μm. Thickness of the whole multilayer is of 150 μm to 200 μm, preferably of 170 μm to 190 μm. A 4-layer metalized silicone with silicone cover, containing traces on different individual layers but all terminated with pads on outer cover surface has a thickness of 215 μm to 245 μm, preferably of 225 μm to 235 μm. The electrode pad has a cross section of 160 μm to 230 μm, preferably of 190 μm to 210 μm.

Figure 1A:
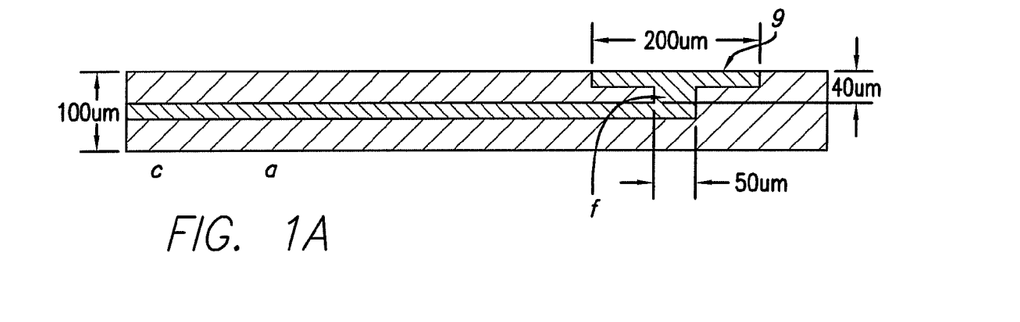
FIG. 1A presents a cross-sectional view of one layer metalized silicone with a pad.

FIG. 1A presents a cross-sectional view of one layer metalized silicone with a pad. It has a thickness of 90 μm to 110 μm and contains metalized silicone sheeting with a silicone cover; traces are connected to pads on the outer cover surface.

Figure 2:
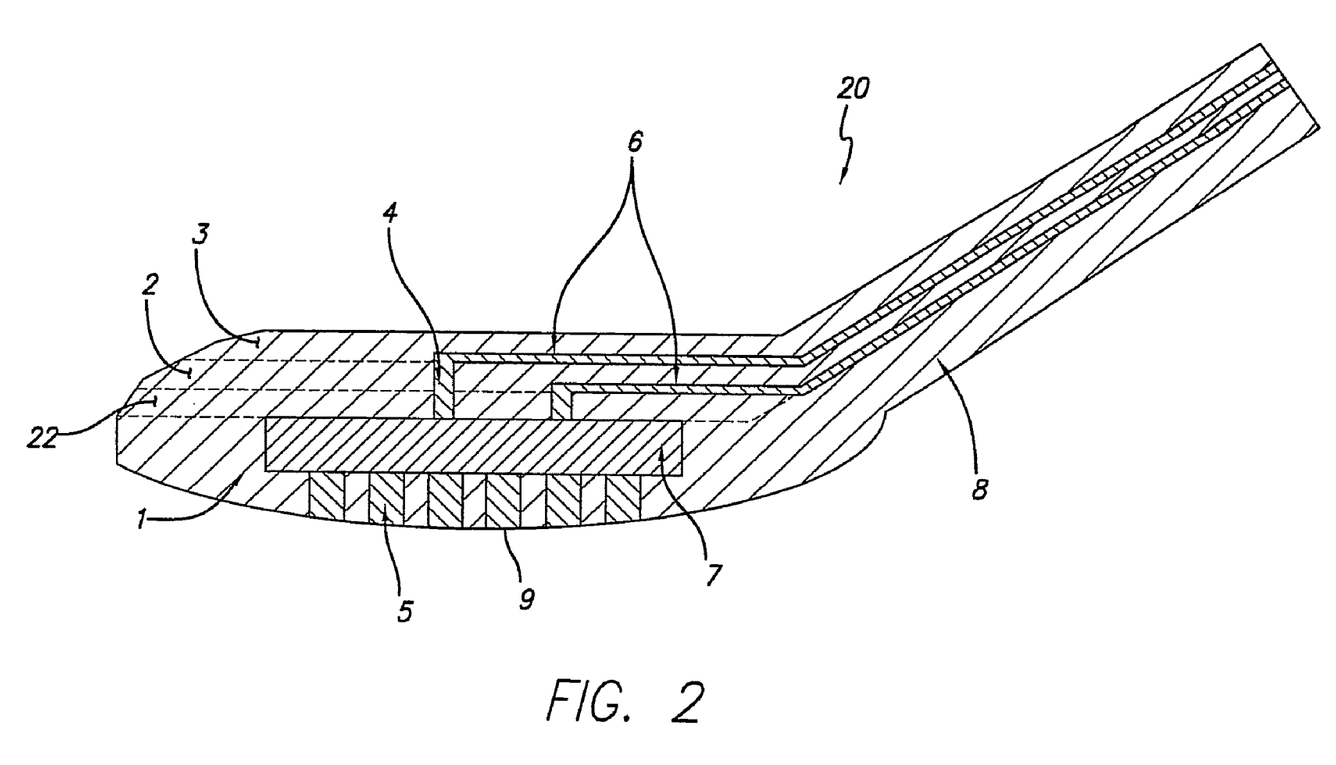
FIG. 2 presents a cross section of visual prostheses.

FIG. 2 presents a cross section of visual prostheses. FIG. 2 shows a convex molded base silicone piece 1 with a radius of 10 mm to 15 mm, preferably 12 mm. Metalized planar silicone containing layers 2 are provided on base silicone piece 1. A non-metalized silicone cover 3 is provided on the top. Vias 4 are laser-drilled through planar silicone cover layers 2 and 22, contacting demux IC 7 on one end and contacting Pt traces on the other end. A demux IC 7 is embedded in base silicone piece 1. Pt-vias 5 are laser-drilled through base silicone piece 1, contacting demux IC 7 on one end, and terminating on the other end with Pt-pads on curved base silicone piece 1, these pads being designed for contacting retina. Pt traces 6 are on the surface of each planar metalized silicone cover layer. Silicone cable 8 contains embedded Pt traces 6.

Figure 3:
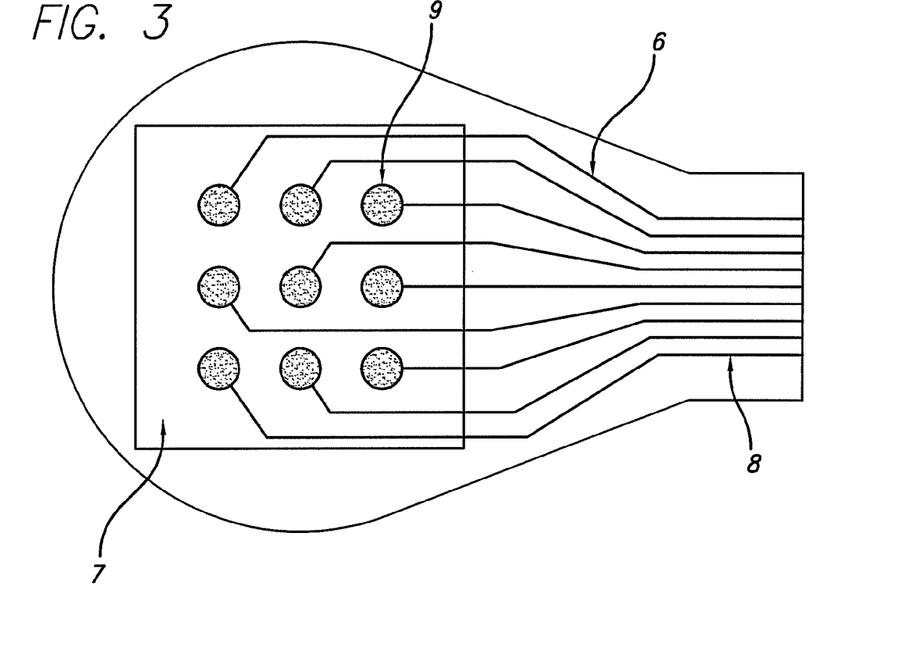
FIG. 3 presents the back view of visual prostheses as shown in FIG. 2.

FIG. 3 presents the back view of a visual prostheses as shown in FIG. 2. FIG. 3 presents embedded back Pt electrode pads 9. Each electrode pad 9 is connected to embedded demux IC 7 and one trace 6 of embedded Pt traces. Silicone cable 8 contains Pt traces 6.

Figure 4:
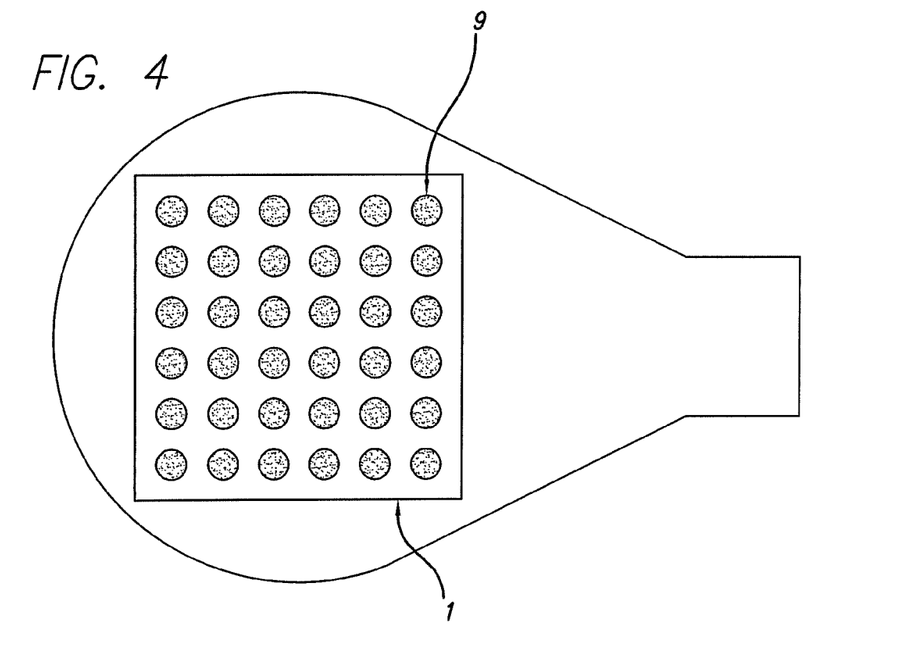
FIG. 4 presents the front view of visual prostheses as shown in FIG. 2.

FIG. 4 presents the front view of visual prostheses as shown in FIG. 2. FIG. 4 presents open electrode pads 9. Each of the open front electrode pads (e.g. 36 in FIG. 4), are connected to demux IC 7 and contact the retina.

Figure 5:
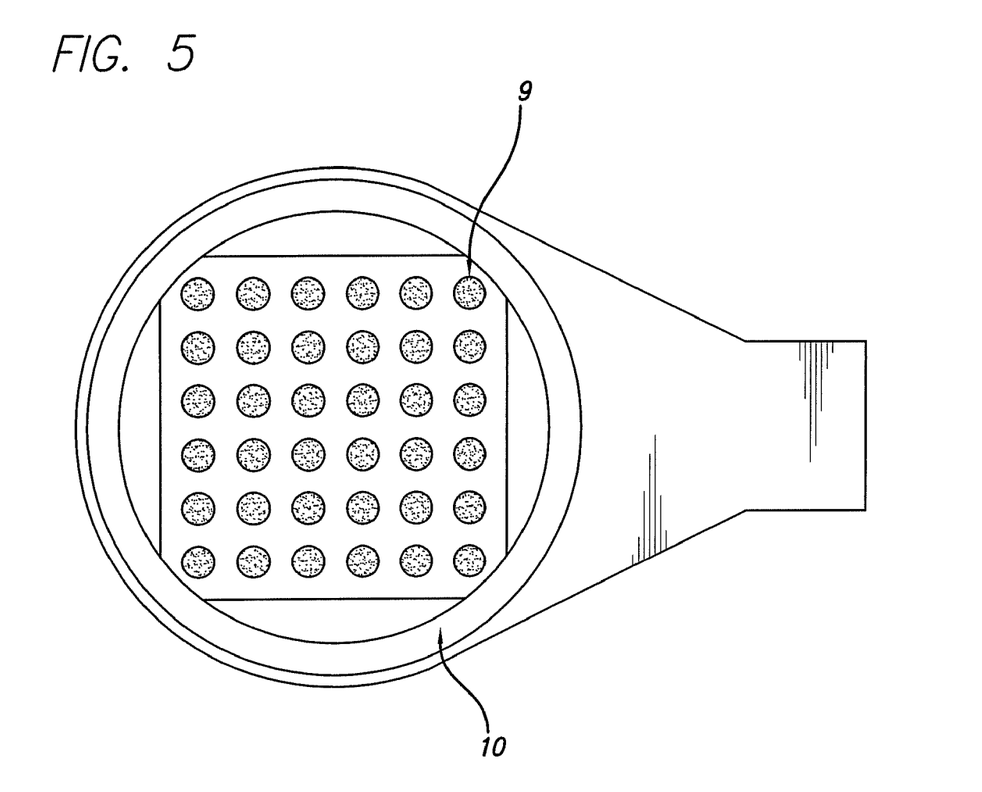
FIG. 5 presents the front view of visual prostheses as shown in FIG. 2 to be attached to the retina by biological glue.

FIG. 5 presents the front view a visual prostheses as shown in FIG. 2 to be attached to the retina by biological glue 10.

Figure 6:
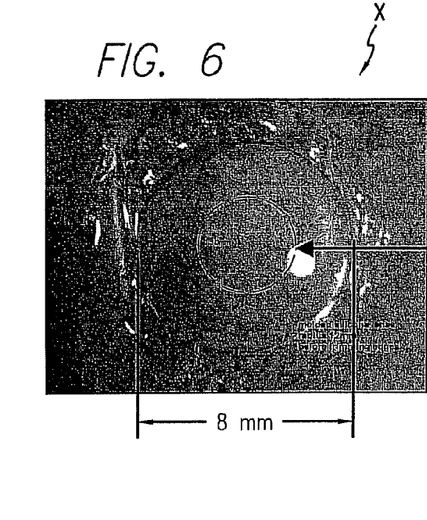
FIG. 6 presents the front view of a molded silicone.

FIG. 6 presents the front view of a molded silicone. The molded plano-convex silicone lens is shown before trimming edges; image shows convex surface. The cross section is between 6 mm and 12 mm thick, preferably between 7 mm and 9 mm.

Figure 7:
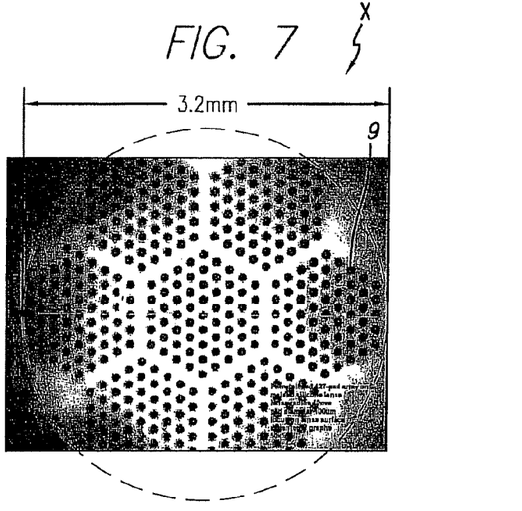
FIG. 7 presents the front view of a molded silicone as presented in FIG. 6 with electrodes.

FIG. 7 presents the front view of a molded silicone as shown in FIG. 6 with electrode pads 9. The cross section is between 2.8 mm and 3.4 mm, preferably 3.1 mm and 3.3 mm. It shows exemplary 427 Pt electrode pads 9 (about 100 μm diameter and about 100 μm spacing, regularly distributed over a 3.2 mm diameter area on top of a 12 mm radius spherical silicone lens.

Figure 7A:
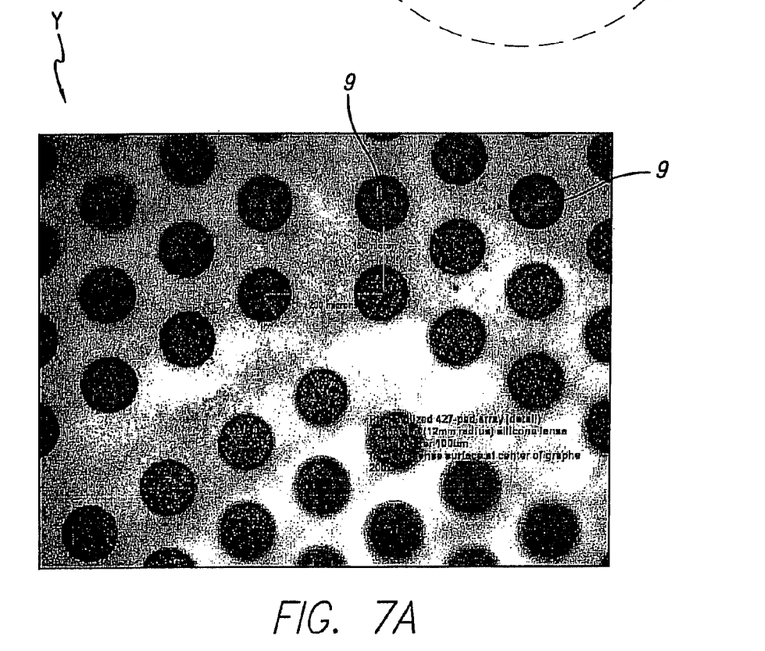
FIG. 7A presents a magnification of the metalized front view of a molded silicone as presented in FIG. 7.

FIG. 7a presents a magnification of the metalized front view of a molded silicone as shown in FIG. 7 with 427 circular Pt electrode pads 9 on a molded silicone lens having about 100 μm diameter and about 100 μm spacing.

Figure 8:
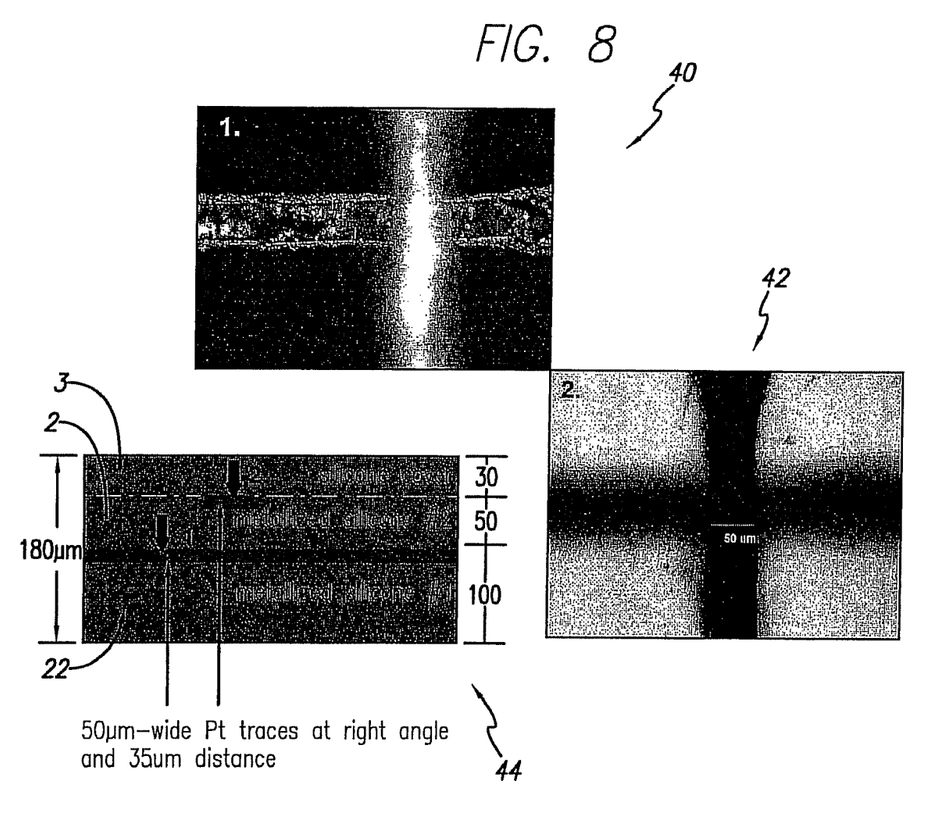
FIG. 8 presents a cross sectional view of a silicone layer with two metal trace layers; photomicrograph 40 shows the a top view on trace 1 and photomicrograph 42 shows a top view on trace 2.

FIG. 8 presents a cross-sectional view of a silicone layer with two metal trace layers; photograph 40 shows a top view on trace 1 and photograph 42 presents a top view on trace 2. 2-layer metalized silicone with a thickness of 150 μm to 200 μm, preferably 170 μm to 190 μm, with silicone cover of about 30 μm to 70 μm, preferably 45 μm to 55 μm distance between Pt traces and about 40 μm to 60 μm, preferably 30 μm to 35 μm silicone between traces. The measured resistance is about R=16 Ω/cm. It shows 40 μm to 60 μm, preferably 45 μm to 55 μm wide Pt traces at right angle and 25 μm to 45 μm, preferably 30 μm to 40 μm distance. Picture 1 focuses on a trace at bottom layer (R-light). Picture 2 focuses on a trace at top layer (T-light).

Figure 9A:
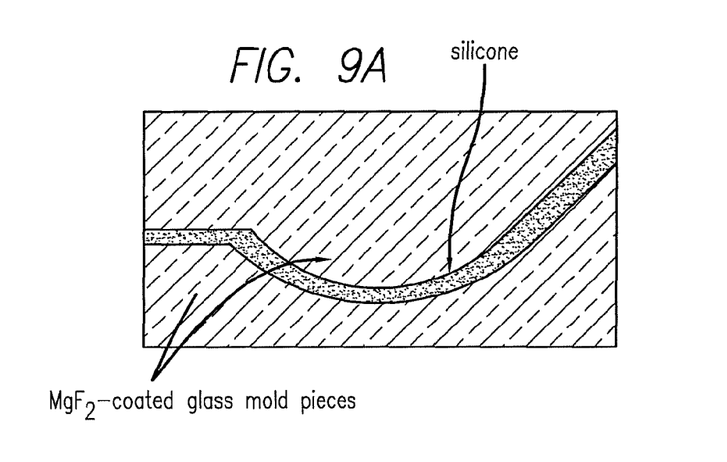
FIGS. 9A to 9F present a sequence for manufacturing a curved metalized electrode array.
Figure 9B:
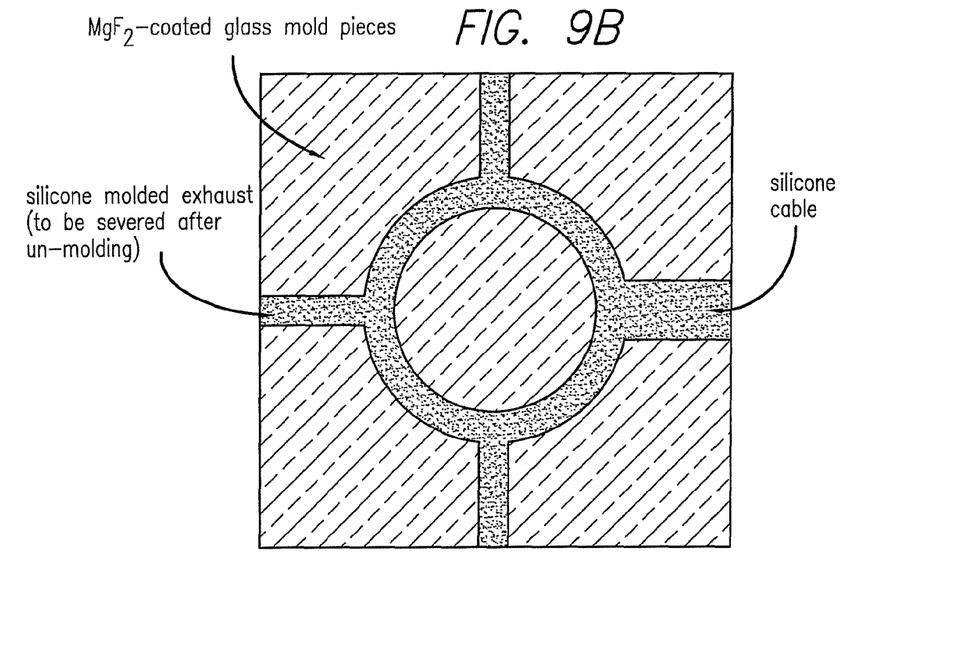
Figure 9C:
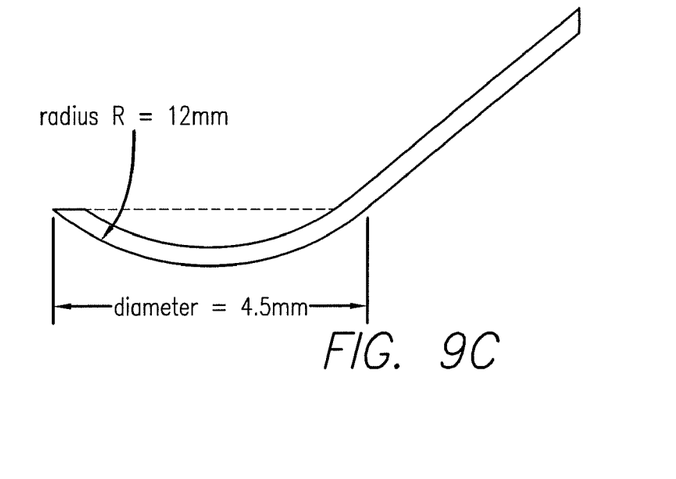
Figure 9D:
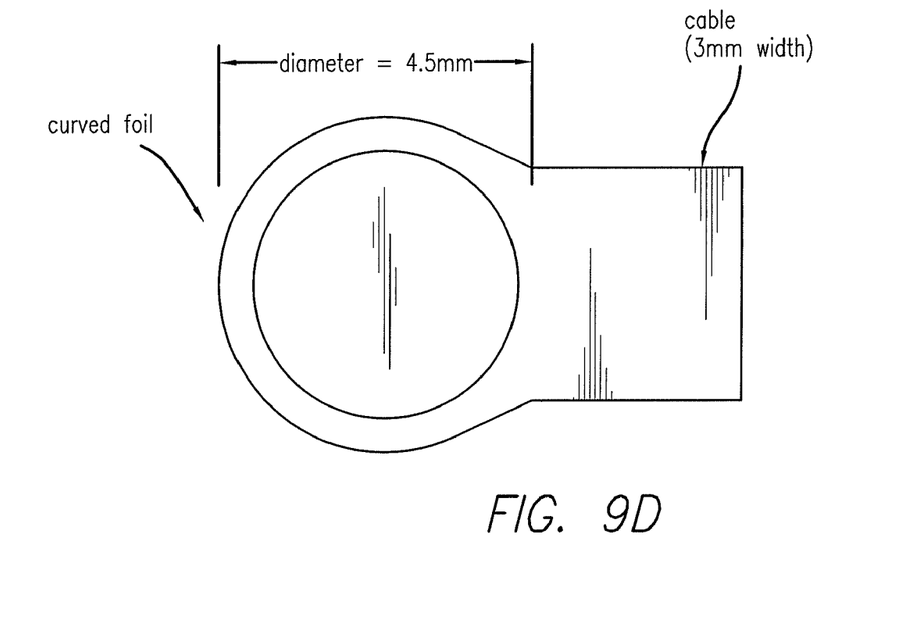
Figure 9E:
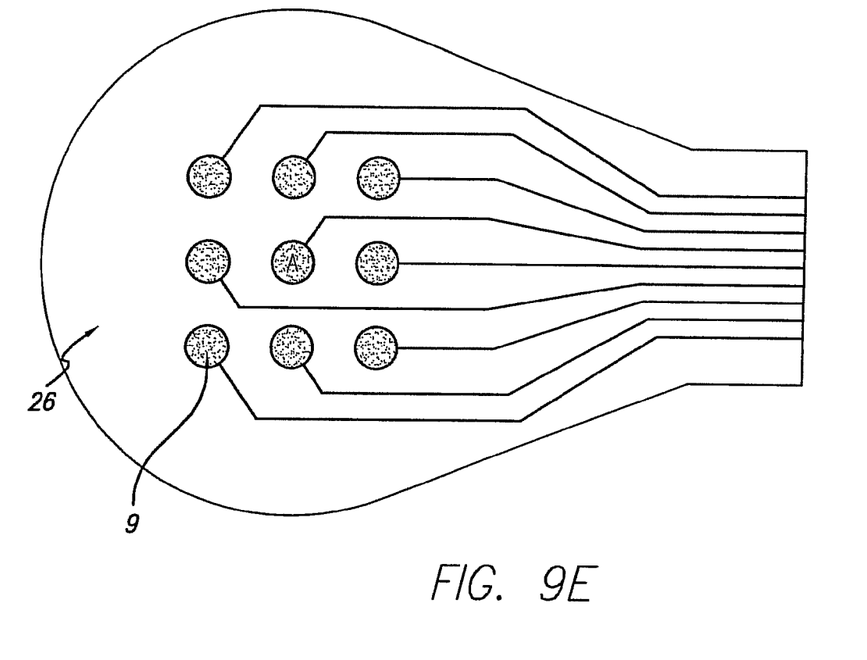
Figure 9F:
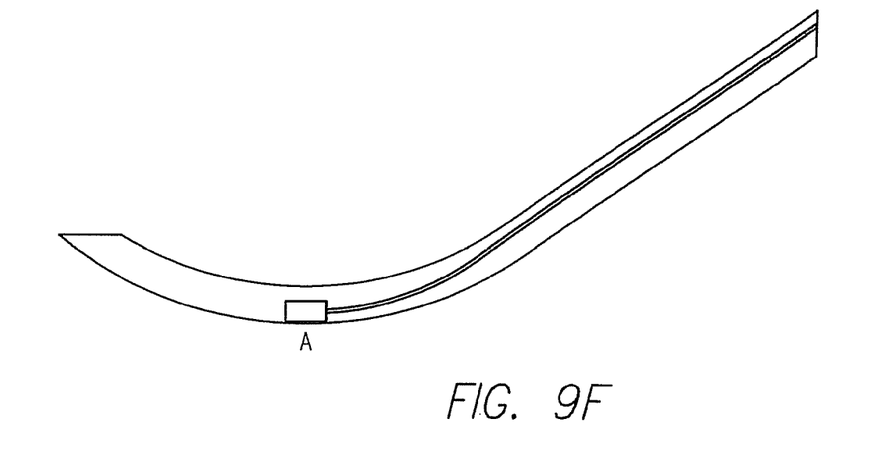
Figure 11:
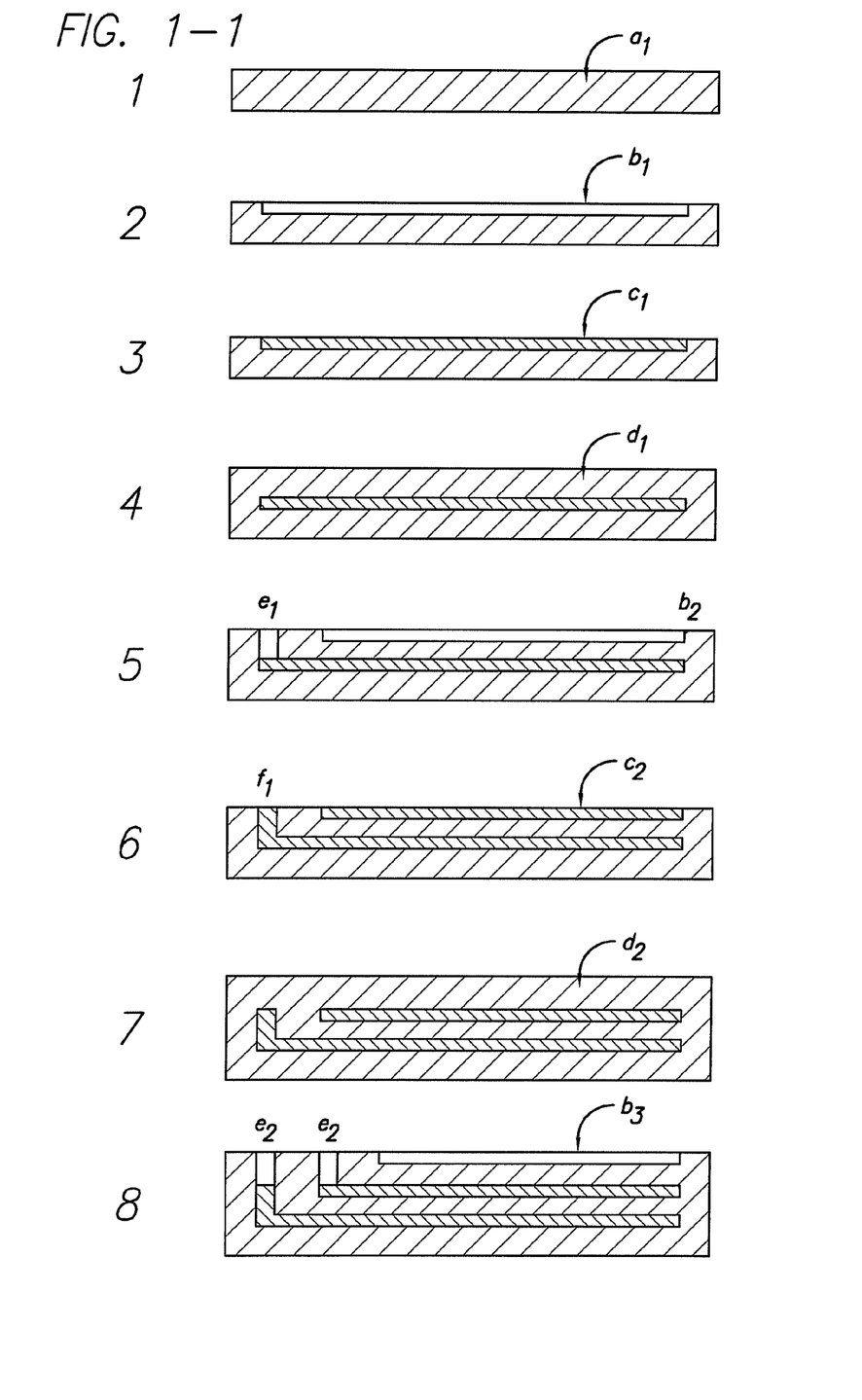
Figure 12:
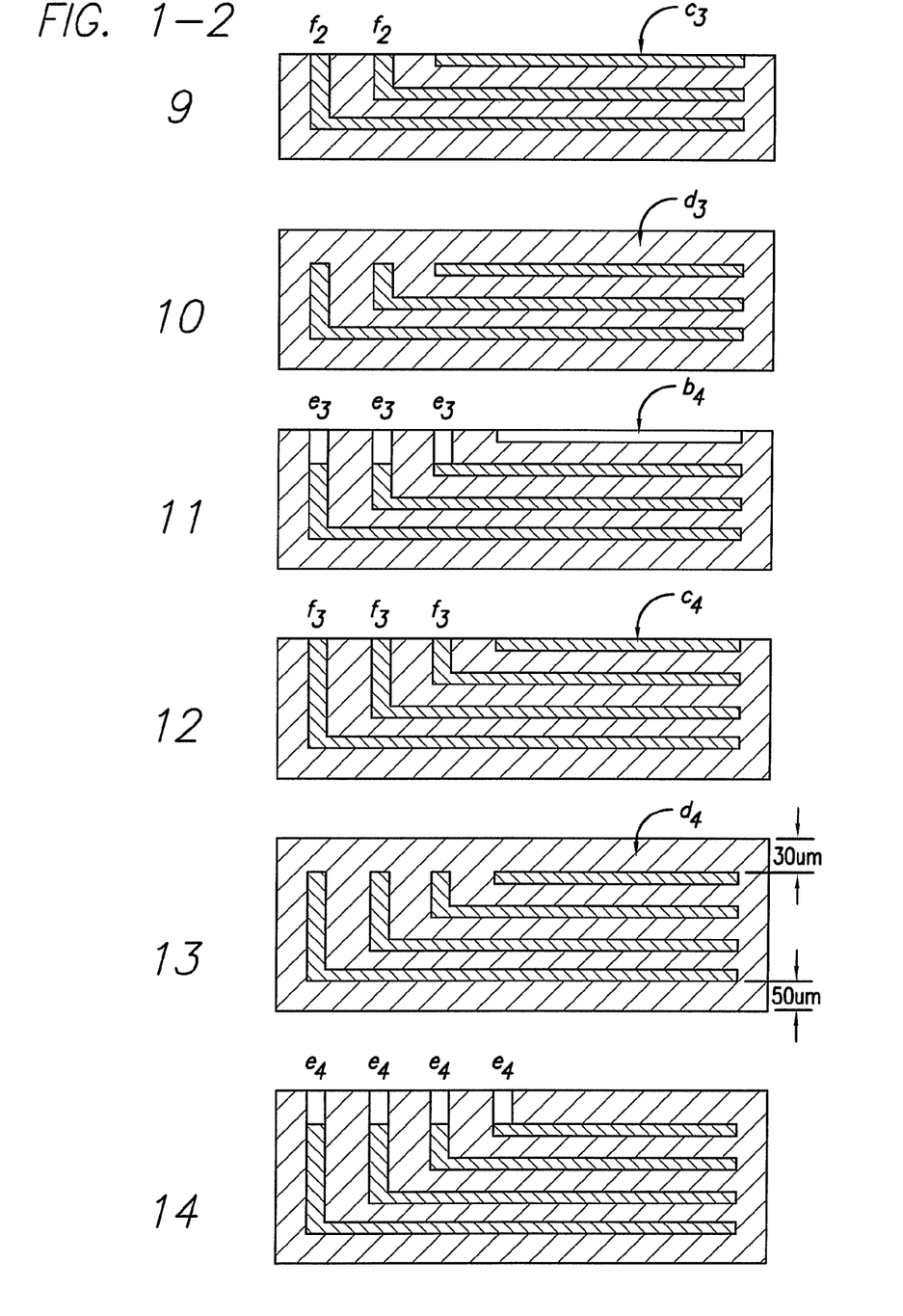
Figure 13:
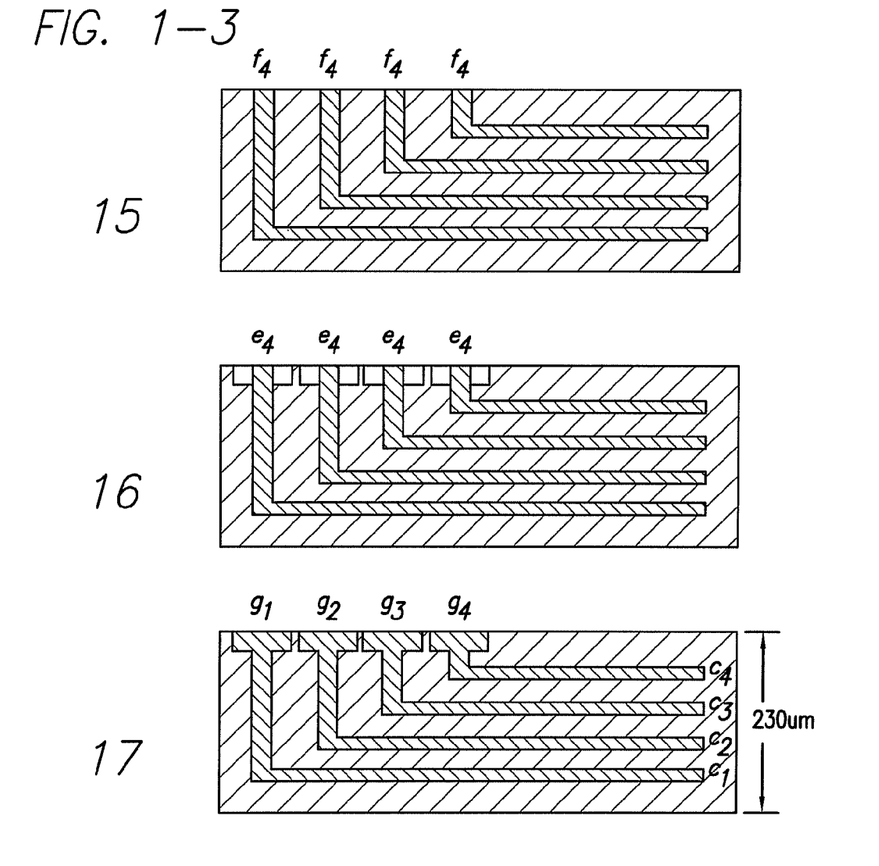

FIGS. 9A to 9F present a sequence for manufacturing a curved metalized electrode array. FIG. 9A presents a cross-sectional view of FIG. 9B along the dotted line and the step of molding silicone between two MgF$_2$-coated glass mold pieces. Silicone is poured on the base glass piece of the form and subsequently the top glass piece is mounted together with the base part. After silicone is cured at a temperature of 150° C. to 180° C., for 10 to 20 minutes, base and top glass pieces are separated yielding a silicone piece as presented in FIGS. 9C and 9D. The molded silicone is metalized. The metalizing method is carried out as described in previous sections. The curved metalized surface is covered with a layer of silicone using the same molding tool containing MgF$_2$-coated base and top glass pieces. The pad areas, as shown in FIG. 9F, are further opened by laser irradiation.

Examples of Producing a Molded Base Silicone Piece

1. Plano-Convex Lens

A plano-concave fused silica lens is coated with a MgF$_2$ thin layer on its concave face. The latter is filled with a silicone material that is appropriate for molding applications (i.e. containing silica foam). Filling should exceed the volume of the concave face. The silicone is further compressed with a MgF$_2$-coated fused glass plate. Compression is exerted along the optical axis of the lens in such a way that silicone would overflow over the edge of the lens. The two fused silica piece assembly containing silicone is maintained under compression while placed in an oven for curing silicone. When curing is complete, the two fused silica piece assembly is separated and the molded silicone piece (forming a plano-convex lens) is extracted by peeling; as allowed by the MgF$_2$ coatings that are present on the fused silica piece assembly.

The actual radius of the molded piano-convex silicone lens equals the one of the plano-concave fused silica molding piece. That radius may be adjusted to any given value, as a function of the planned application. In particular, it may be equal to the human eyeball radius of 10 mm to 15 mm, preferably about 12 mm. In that way, the whole curved (concave) surface of the silicone lens may precisely contact the human retina.

2. Concave-Convex Lens

A piano-concave fused silica lens, its concave surface having a radius of curvature, R, is coated with a MgF$_2$ thin layer on its concave face. An annular spacer is positioned on the outer edge of the concave face. The annular spacer is made of either metal or any dense polymeric material. Its thickness may be adjusted to a desired value, e.g. 100 μm. The concave face of the lens is then filled with a silicone material that is appropriate for molding applications (i.e. containing silica foam). Filling should exceed the volume of the concave face. The silicone filling is further compressed with $MgF_2$-coated fused silica convex surface having the same radius of curvature, R, as the plano-concave lens above. Advantageously, the latter may belong to a piano-convex lens.

The silicone is compressed until the compressing convex surface reaches the spacer surface. While maintaining compression, the assembly is brought into an oven to cure silicone. After curing is completed, the two lenses are separated and the molded silicone piece (now a thin molded silicone foil in the form of a double-sided convex-concave lens) is peeled from the $MgF_2$-coated fused silica surfaces. Further, edge trimming the above molded piece may be performed with an excimer laser working at either 248 nm or, preferably, 193 nm. Object trimming is to remove all unnecessary parts of the molded piece and to fit its final geometry to the application requirements. The thickness of this molded silicone piece is equal to the spacer thickness. During manipulation, it retains the integrity of its curved geometry. The actual radius, R, may be adjusted to equal the radius of the human eyeball. In so doing, the convex surface of the resulting trimmed curved silicone piece may be brought to intimate contact with the retina.

After the molded silicone piece has been fabricated, its convex surface is laser-processed to a desired geometry and further metalized with pads and traces as required by the application.

Further to the metallization, the resulting metalized piece is covered with a silicone layer. This covering is performed in the following manner:

Case of a plano-convex silicone piece:

The metalized silicone piece is positioned on a $MgF_2$-coated fused silica plate, its flat surface contacting the plate; an annular spacer is positioned around the molded piece; this spacer may be metallic or polymeric, its thickness is usually 50 μm but may be varied; the metalized, curved surface of the silicone piece is then covered with a drop of silicone; a $MgF_2$-coated concave lens having the same radius of curvature as the metalized silicone surface is now used to compress the silicone drop onto the molded silicone piece; compression is applied until reaching the spacer surface and further maintained while bringing the assembly into the oven for curing the silicone cover; after curing is completed, the whole silicone piece, imbedding the metalized parts as described above, is separated from the two fused silica parts. Lastly, laser edge-trimming of the resulting silicone piece is performed to adjust its geometry.

Case of a concave-convex silicone piece:

The metalized silicone piece is placed on a $MgF_2$-coated convex fused silica lens having the same radius of curvature R as its (non-metalized) concave surface, the latter facing the convex surface of the lens; an annular (metallic or polymeric) spacer is positioned on the edge of the opposite (metalized) surface of the silicone piece; the latter is then covered with a drop of silicone. A $MgF_2$-coated concave fused silica lens having a radius of curvature, R, is used to compress the silicone drop onto the metalized surface of the silicone piece; compression is applied until reaching the surface of the spacer, and is further maintained while placing the assembly into an oven for curing the silicone cover. After curing is complete, the whole molded silicone piece, now embedding metalized parts, is peeled from the fused silica parts and laser edge trimmed.

Advantageously, both for simplicity and for a perfect integration of the materials in contact, the same silicone material may be used for the base substrate (to be laser-processed and further metalized) and the cover. Identically, the same curing procedure is applied for both the silicone base and its cover. In so doing, a perfect integration of the assembled silicone piece is achieved that guarantees perfect imbedding of the metalized parts.

Further, the cover layer is now laser-processed and metalized along traces and pads as described above. It is covered with an additional layer of silicone that can be laser-processed, metalized and silicone-covered as many times as desired. The process is extended to the production of a curved, multi-layered metalized silicone structure, containing a stack of either identical or other metalized silicone layers, all being covered with a final plain silicone film. Each individual silicone layer in the stack has a thickness of about 50 μm, except for the last (un-metalized) silicone cover which has a thickness of 30 μm.

$MgF_2$-coated fused-silica lenses (either spherical or cylindrical) are known market products that are used in all ultraviolet optical settings. Since their surfaces are polished to perfection, the above described fabrication offers excellent cost-effective silicone products that can be adapted to the desired application. Other means of molding may be devised that would not depart from the above procedures, in particular using custom-made molds that are comprised of $MgF_2$-fused silica or metal.

Example of Protective Coating

Upon laser-irradiation with a pulsed UV laser source (e.g., an excimer laser source working at 248 nm), silicone is partially decomposed. Along with irradiation, residue of the decomposition is ejected from the laser-processed areas and lands lateral to these areas. Such residue consists of broken molecular segments of the polymeric silicone material and is, therefore, rich in structural defects. These defects are electrically active atomic sites. They may chemically fix metal ions during immersion of the laser-processed silicone in an electroless autocatalytic solution. The solution is the type used for metalizing the laser-processed silicone areas. If residue is present during immersion, metallization follows on areas that do not correspond to the desired areas that have been laser-processed. Therefore, these defects must be removed from silicone after laser-irradiation and before immersion in a metallization bath. Removal may be performed by depositing on silicone and before laser-irradiation a film of material that is removed from the silicone surface after irradiation and that carries away all such residues. To be useful, the laying of the film as well as its removal should not alter the silicone surface chemically or physically. This is achieved by depositing a film of soap onto silicone, wherein a solution of soap is first formed by dissolving soap in water. After adjusting the viscosity of the solution, a film of soap is formed by knife-coating a silicone layer. Upon drying off, a film of soap is formed with a thickness of 2 μm all over the silicone surface. Laser-irradiation of the soap-coated silicone layer is then performed along a trace of 20 μm width. Residues are ejected on both sides of the trace, up to 50 μm from its edges and agglomerate on the soap film. The silicone piece is then washed thoroughly with distilled water. The soap film is dissolved and all residues are carried away by water streaming. The silicone piece is thus cleaned of the residue, and the actual laser-processed trace remains devoid of lateral defects. Upon immersion in an electroless metallization solution, metallization is restricted solely to the actual trace width that was cut by the laser beam.

Example of Retinal Contact Lens Process Method

Each electrode pad 9 that faces the retina needs to be polarized, Increasing the number of electrode pads has the direct consequence of increasing the number of traces 6 that traverse the eyeball, as well increasing power supply needs and heat generation.

A way to reduce the number of traces (by one-quarter) is to use a de-multiplexing integrated circuit (IC) (Demux) within the eyeball. A molded silicone lens may be used to that end.

the curved space of a concave $MgF_2$-coated fused silica lens (radius of curvature equal to 12 mm, the radius of a human eyeball) is filled with silicone; an integrated circuit (IC), coated with an $SiO_2$ insulating coating, is pressed into the silicone filling along the axis of the lens; a further covering of the IC is performed with silicone; finally a $MgF_2$-coated fused silica plate is pressed onto silicone along the lens axis; while compression maintained, the assembly is placed in an oven for curing silicone; after curing is completed, the cured silicone piece, now imbedding the IC, is recovered by separating the silica pieces; that silicone piece has one curved (convex) surface and one flat surface;

This follows the laser-processing of the silicone piece containing the IC and adapting it to forming a retinal implant.

vias (e.g., 50 µm in diameter, at 300 µm pitch) are driven through the convex silicone surface and through the IC $SiO_2$ coating down to the silicon (Si) surface of the IC by using the 193 nm excimer laser source; these vias are Pt-metalized by electroplating; they are further equipped with 200 µm-diameter end-pads that are produced by 248 nm laser-irradiation of the curved silicone surface; these pads are further Pt-metalized via electroless autocatalytic metallization;

using the same 193 nm excimer laser source, vias are placed through the flat silicone layer that covers the other side of the IC; these vias are metalized by electroplating; traces are further drawn onto the silicone layer and connected to the vias; lastly the traces are metalized by electroless metallization forming a set of traces on the flat silicone surface;

another layer of silicone is placed on the flat silicone surface containing the traces; that layer may serve as a protective cover to the set of metal traces; it alternatively may further laser-processed and metalized with a new series of traces that connect each to a new via onto the IC surface underneath. The procedure may be repeated as many times as necessary in order to interconnect all the pads that are present on the curved surface of the piece.

Example for Metallization of Silicone

2. Protective Coating with Soap

A silicone sheet (NuSil MED 4950 from NUSIL TECHNOLOGY LLC, Carpinteria, Calif.) having a thickness of 80 µm was knife coated with a 2 µm thick soap layer.

2. Removal of Protective Soap Coating:

The silicone sheet is rinsed in de-ionized water several times to dissolve the soap layer and to dry it.

3. Metallization

The silicone sheet was mounted on a glass cylinder. The glass with the silicone sheet is immersed in the same metalizing solution in a temperature controlled vessel for 3 to 5 hours. From time to time (e.g., every 10 minutes), $H_2$ bubbles are eliminated from the sheeting by vibrating the cylinder or by heat flashing the silicone sheet. The silicone sheet is rinsed in distilled water at the end of the procedure.

The soap coating allowed the irradiation residue, that are generated during irradiation.

In step two, a glass cylinder and a temperature controlled vessel are specifically designed for this purpose. The present invention provides the metalizing of an expanded silicone layer for enhanced metal embedding. A silicone layer is applied on a glass cylinder. After inscribing the laser-processed traces on the convex, expanded silicone surface, the silicone layer on the glass cylinder is placed in an electroless platinum (Pt) bath for metallization of the traces. The metalized silicone layer is detached from the glass cylinder and recovers its original planar geometry. The expanded platinum (Pt) traces contract, enclosing the metal parts into silicone and providing an enhanced integration of these traces into the silicone layer. The once-expanded platinum (Pt) traces, at the time of their production, contract and enclose the metal parts in the silicone, providing enhanced integration of these traces into the silicone layer.

While the invention has been described by means of specific embodiments and applications thereof, it is understood that numerous modifications and variations may be made by those skilled in the art without departing from the spirit and scope of the invention. It is to be understood that within the scope of the claims, the invention may be practiced otherwise than as specifically described herein.

What is claimed is:

1. A flexible electrode array comprising one silicone containing base layer and one silicone containing cover layer, and at least one platinum trace layer embedded in said silicone containing base layer.

2. The flexible electrode array of claim 1 comprising at least one silicone containing layer between said one silicone containing base layer and said one silicone containing cover layer.

3. The flexible electrode array of claim 1 comprising one metal trace between said one silicone containing base layer and said one silicone containing cover layer.

4. The flexible electrode array of claim 2 comprising at least two metal traces stacked between said one silicone containing base layer and said one silicone containing cover layer.

5. The flexible electrode array of claim 1 wherein said one silicone containing base layer and said one silicone containing cover layer form a molded polymer body.

6. The flexible electrode array of claim 1 wherein said silicone comprises polydimethylsiloxane.

7. The flexible electrode array of claim 4 comprising 1 to 1000 electrode pads.

8. The flexible electrode array of claim 7 wherein said at least two metal traces and said electrode pads are comprised of uthenium, gold, or alloys or mixtures thereof.

* * * * *